(12) United States Patent
Favero et al.

(10) Patent No.: US 11,746,027 B2
(45) Date of Patent: Sep. 5, 2023

(54) METHOD FOR TREATING AQUEOUS EFFLUENT

(71) Applicant: S.P.C.M. SA, Andrezieux-Boutheon (FR)

(72) Inventors: Cédrick Favero, Andrezieux Boutheon (FR); Morgan Tizzotti, Andrezieux Boutheon (FR); Frédéric Daguerre, Andrezieux Boutheon (FR); Marc-Edouard Michel, Andrezieux Boutheon (FR)

(73) Assignee: S.P.C.M. SA, Andrezieux-Boutheon (FR)

( * ) Notice: Subject to any disclaimer, the term of this patent is extended or adjusted under 35 U.S.C. 154(b) by 270 days.

(21) Appl. No.: 17/185,483

(22) Filed: Feb. 25, 2021

(65) Prior Publication Data
US 2021/0269332 A1 Sep. 2, 2021

(30) Foreign Application Priority Data

Feb. 27, 2020 (FR) .................................... 20 01955

(51) Int. Cl.
| | | |
|---|---|---|
| C02F 1/56 | (2023.01) | |
| C02F 1/52 | (2023.01) | |
| C02F 1/54 | (2023.01) | |
| C08L 33/02 | (2006.01) | |
| C08L 33/26 | (2006.01) | |
| C10G 1/04 | (2006.01) | |
| C02F 103/10 | (2006.01) | |
| B01D 21/01 | (2006.01) | |
| C07C 31/13 | (2006.01) | |
| C07C 43/02 | (2006.01) | |

(52) U.S. Cl.
CPC .............. *C02F 1/56* (2013.01); *C02F 1/5272* (2013.01); *C02F 1/547* (2013.01); *C08L 33/02* (2013.01); *C08L 33/26* (2013.01); *C10G 1/045* (2013.01); *B01D 21/01* (2013.01); *C02F 2103/10* (2013.01); *C02F 2305/04* (2013.01); *C07C 31/13* (2013.01); *C07C 43/02* (2013.01)

(58) Field of Classification Search
None
See application file for complete search history.

(56) References Cited

U.S. PATENT DOCUMENTS

| | | | | |
|---|---|---|---|---|
| 4,176,107 A | * | 11/1979 | Buckman | .................. C08K 5/04 |
| | | | | 523/332 |
| 2019/0367389 A1 | * | 12/2019 | Fenderson | ................. C02F 1/56 |

FOREIGN PATENT DOCUMENTS

CN 110 745 929 2/2020

OTHER PUBLICATIONS

Rao et al. (International Journal of Mineral Processing, 1980, 7, 245-253 (Abstract only). (Year: 1980).*
Preliminary Search Report for FR 2001955 dated Oct. 20, 2020.

* cited by examiner

*Primary Examiner* — Clare M Perrin
(74) *Attorney, Agent, or Firm* — B. Aaron Schulman, Esq.; Stites & Harbison, PLLC (57) ABSTRACT

The invention concerns a flocculation formulation. The invention also concerns the treatment of mine tailings in the form of aqueous effluents comprising solid particles. With the method of the invention, it is possible to separate all or part of the water from an aqueous effluent comprising solid particles.

12 Claims, 4 Drawing Sheets

METHOD FOR TREATING AQUEOUS EFFLUENT

The invention concerns a flocculation formulation. The invention also concerns the treatment of mine tailings in the form of aqueous effluents comprising solid particles. With the method of the invention, it is possible to separate all or part of the water from an aqueous effluent comprising solid particles.

Numerous mining extraction processes produce tailings in the form of aqueous effluent comprising solid particles. For example, the production of hydrocarbons from bituminous or oil sands leads to such mine tailings. The management of tailings is therefore a challenge for the mining industry, in particular since the start of extraction operations from oil sands. It is therefore incumbent upon operators to determine the manner in which to remove these by-products safely and efficiently. The challenge is all the greater owing to the large scale of oil sand production.

In general, mining operations produce such tailings or waste materials in particular when extracting ores for the production of coal, diamonds phosphate or different metals e.g. aluminium, platinum, iron gold, copper, silver etc. Such waste can also result from the conversion of ores or from industrial processes or washing processes.

Mine tailings can take on different forms, slurries in particular. In general, they are suspensions of solid particles in water.

In general, mine tailings from oil sands are therefore composed of water, clay, sand and residual hydrocarbons derived from the extraction process.

Routine industrial practice up until now entails pumping the tailings into vast settling ponds. The heavier material, chiefly sand, deposits on the bottom whilst the water rises to the surfaces and can be recycled. The intermediate layer, known as mature fine tailings (MFT), is generally composed of 70% water and 30% fine clay particles. Left to nature, the layer of mature fine tailings could take centuries to solidify. The continuing development of mining operations has necessitated the creation of an increasing number of settling ponds of ever-increasing size.

The mineral slurries produced by physical or chemical treatment processes of oil sands are therefore stored in open air basins, ponds, retaining dams or backfill in semi-liquid form. These large volumes of stored slurries therefore amount to a true hazard, in particular in the event of dam rupture.

Having particular regard to technical, environmental or regulatory requirements, it is henceforth necessary to find means to accelerate or improve the conversion efficacy of mature fine tailings in robust storage areas that can subsequently be rehabilitated. Soil remediation after mining operations has been made compulsory by environmental legislation. Accelerated treatment of mine tailings is also necessary, in particular by increasing the sedimentation rate thereof for efficient recycling of water and to reduce the volume of these tailings.

In general, the separation and recycling of all or part of the water contained in mining aqueous effluents are essential objectives of a mining operation. Therefore, the processes for treating aqueous effluent comprising solid particles have the essential purpose of improving the yield of water separation in particular with a view to recycling the separated water and to allow easy handling of the final waste. Higher net water release (NWR) is a major target of processes for treating aqueous effluents comprising solid particles.

Methods are known for the physical treatment of these mine tailings, e.g. centrifugation, filtration, electrophoresis and electrocoagulation.

In addition, chemical methods are emerging. For example, methods are known which involve the addition of chemical products such as sodium silicate, organic flocculants, inorganic coagulants, oxidizing agents, reducing agents or carbon dioxide. The use is also known of synthetic or natural polymers as coagulants or flocculants, to separate the solids from the liquid.

Natural surfactants such as naphthenic acids are widely contained in process waters derived from the extraction of oil sands. Paying heed to a «zero waste» policy, process waters cannot be discharged into the environment and are continually recycled and reused for bitumen extraction processes (Xue et al. Sci. Total Environ. 2018, vol. 627, 916-933). On this account, the concentration of naphthenic acids in process waters has continually increased over the last forty years (Chongchong et al. Fuel 2019, vol. 253, 1229-1246), reaching concentrations estimated to be 40-120 mg/L (Al Jibouri et al. J. Process Control. 2018, vol. 66, 1-11) and causing the production water to foam easily and complicate the dissolving of flocculants on industrial scale.

The problem to be solved is lubrication of the polymer at the grinding step and prevention of the presence of foaming at the time of polymer dissolution, the polymer being in powder form.

In a first aspect, the invention concerns a flocculation formulation comprising:
at least one flocculating agent, said agent being a copolymer prepared from at least one nonionic monomer and at least one anionic monomer;
at least one surfactant selected from among fatty acid esters;
at least one additional compound of formula (I):

Formula I where:
R1 is a hydrogen atom or a saturated or unsaturated, linear, branched, aromatic or cyclic carbon radical having X carbon atoms of between 3 and 20;
R2 is a saturated or unsaturated, linear, branched, aromatic or cyclic carbon radical having Y carbon atoms of between 3 and 20;
and X+Y=6 to 30 carbon atoms.

Numerous compounds can be used as flocculating agent for the method of the invention. In particular, it is a copolymer prepared from at least one nonionic monomer and from at least one anionic monomer. Optionally, the copolymer is also prepared from at least one cationic monomer and/or at least one monomer of hydrophobic nature.

The nonionic monomer(s) able to be used in the invention can be selected in particular from the group comprising water-soluble vinyl monomers. Preferred monomers belonging to this class are for example: acrylamide, methacrylamide; N-isopropylacrylamide; N,N-dimethylacrylamide; N, N diethylacrylamide; N-methylolacrylamide; N-vinylformamide; N-vinyl acetamide; N-vinylpyridine; N-vinylpyrrolidone; acryloyl morpholine (ACMO), glycidyl methacrylate, glyceryl methacrylate and diacetone acrylamide. One preferred nonionic monomer is acrylamide.

The nonionic monomer(s) are preferably used in an amount ranging from 50 to 90 mole %, more preferably from 30 to 45 mole %, relative to the total number of moles of monomers.

In the invention, the particularly preferred copolymer is a copolymer prepared from acrylamide.

In the invention, the particularly preferred flocculating agent is a copolymer prepared from acrylamide.

The anionic monomer(s) able to be used in the invention can be selected from among monomers comprising at least one carboxylic acid function; monomer salts comprising at least one carboxylic acid function; monomers comprising at least one sulfonic acid function; monomers comprising at least one phosphonic acid function; monomer salts comprising at least one phosphonic acid function.

The anionic monomer(s) are preferably used in an amount ranging from 10 to 70 mole %, preferably ranging from 20 to 55 mole %, relative to the total number of moles of monomers.

As examples of anionic monomers selected to prepare the flocculating agent of the invention, mention can be made of acrylic acid, methacrylic acid, itaconic acid, crotonic acid, maleic acid, fumaric acid, 2-acrylamido-2-methylpropanesulfonic acid, vinylsulfonic acid, vinylphosphonic acid, allylsulfonic acid, allylphosphonic acid, styrenesulfonic acid and the corresponding water-soluble salts. The water-soluble salts of these anionic monomers are typically salts of an alkali metal, an alkaline-earth metal and ammonium. The particularly preferred anionic monomers are acrylic acid, 2-acrylamido-2-methylpropanesulfonic acid and the corresponding salts thereof.

Optionally, the flocculating agent is a copolymer also prepared from at least one cationic monomer.

The cationic monomer(s) able to be used in the invention can be selected from among the salts of diallyldialkyl ammonium; the acidified or quaternized salts of dialkylaminoalkyl acrylates; the acidified or quaternized salts of dialkylaminoalkyl methacrylates; the acidified or quaternized salts of dialkyl-aminoalkylacrylamides and the acidified or quaternized salts of dialkyl-aminoalkylmethacrylamides.

The cationic monomer(s) are preferably used in an amount ranging from 0.01 to 10 mole %, preferably ranging from 0.1 to 4 mole % relative to the total number of moles of monomers.

As examples of cationic monomers selected to prepare the flocculating agent of the invention, mention can be made of diallyldimethylammonium chloride (DADMAC), dialkylaminoethyl acrylate (ADAME), dialkylaminoethyl methacrylate (MADAME), acrylamido-propyl trimethyl ammonium chloride (APTAC), methacrylamido-propyl trimethyl ammonium chloride (MAPTAC).

The acidified salts can particularly be obtained via protonation. The quaternized salts can be obtained by reaction with benzyl chloride, methyl chloride (MeCl), aryl, alkyl chlorides or dialkyl sulfates such as dimethyl sulfate.

Optionally, the flocculating agent is a copolymer also prepared from at least one monomer of hydrophobic nature.

The monomer(s) of hydrophobic nature able to be used in the invention can be selected from among the esters of acrylic acid comprising an alkyl, arylalkyl or ethoxylated chain; the esters of methacrylic acid comprising an alkyl, arylalkyl or ethoxylated chain; the derivatives of acrylamide comprising an alkyl, arylalkyl or dialkyl chain; the derivatives of methacrylamide comprising an alkyl, arylalkyl or dialkyl chain. When use is made of a monomer of hydrophobic nature to prepare the flocculating agent, the amount thereof can range from 0.001 to 3 mole % relative to the total number of monomers.

Preferably, the copolymer of the invention is prepared from at least one nonionic monomer and from at least one anionic monomer, for example in a molar proportion of 70% of at least one nonionic monomer and 30% of at least one anionic monomer.

Also preferably, the molecular weight of the flocculating agent ranges from 3 to 40 million g/mol. Similarly, the molecular weight of the flocculating agent can range from 5 to 30 million g/mol.

By molecular weight, it is meant the weight average molecular weight (Mw). Molecular weight is determined with standard methods such as gel permeation chromatography (GPC). For example, the average molecular weight can be determined with conventional calibration techniques using acetate and the following columns: TSK PWXL (Grade+G6000+G3000). Polyethylene oxide and polyethylene glycol standards can be used to calibrate the columns.

Molecular weight is determined by the intrinsic viscosity of the (co)polymer. Intrinsic viscosity can be measured with methods known to those skilled in the art and can be calculated from values of reduced viscosity for different concentrations of (co)polymer on a graph plotting the values of reduced viscosity (Y-axis) against concentration (X.axis) and by extrapolating the curve to zero concentration. The value of intrinsic viscosity is given on the Y-axis or using the least squares method. Molecular weight can then be determined using the Mark-Houwink equation:

$$[\eta] = K\, M^{\alpha}$$

$[\eta]$ represents the intrinsic viscosity of the (co)polymer as determined by the method measuring viscosity in solution.
K represents an empirical constant.
M represents the molecular weight of the (co)polymer.
$\alpha$ represents the Mark-Houwink coefficient.
K and $\alpha$ are dependent on the particular (co)polymer-solvent system.

The (co)polymers used in the method of the invention as flocculating agent can be (co)polymers of different forms. In particular, they may be branched (co)polymers, preferably (co)polymers branched when polymerizing the monomers used for preparation thereof. At the time of polymerization, it is possible to use a branching or crosslinking agent, and optionally a polyfunctional transfer agent. As branching or crosslinking agent, mention can be made of the compounds selected from among methylene-bis-acrylamide (MBA), ethylene glycol diacrylate, poly(ethylene glycol) dimethacrylate, vinyloxyethyl acrylate, vinyloxyethyl methacrylate, triallylamine, glyoxal, compounds of glycidyl ether type such as ethylene glycol diglycidyl ether, compounds comprising at least one epoxy function, trimercaptotriazine, polyvinyl alcohols, polyvinylamines. The amount of branching or crosslinking agent used generally less than 4 weight % relative to the quantity of monomers.

The additional compound is composed of at least one compound of formula (I):

Formula I where:
R1 is a hydrogen atom or a saturated, unsaturated, linear, branched, aromatic or cyclic carbon radical having X carbon atoms of between 3 and 20;
R2 is a saturated or unsaturated, linear, branched, aromatic or cyclic carbon radical having Y carbon atoms of between 3 and 20;
and X+Y=6 to 30 carbon atoms.

By «carbon radical» it is meant a radical chain only comprising carbon atoms and hydrogen atoms.

More preferably, X+Y is between 8 and 28, more preferably between 10 and 26.

Preferably, the additional compound comprises at least 2 different compounds of formula (II) and (III):

Formula II where m and m' are equal or differ and are each between 3 and 9, preferably between 4 and 8.

Formula III where n is between 5 and 8, preferably between 6 and 7.

The surfactant is selected from among fatty acid esters. The surfactant can be selected from among sorbitan monostearate, sorbitan tristearate, sorbitan monolaurate, sorbitan monooleate, sorbitan monopalmitate, sorbitan trioleate, or the mixtures thereof. Preferably, the surfactant is sorbitan monolaurate.

The additional compound/surfactant weight ratio is between 20:1 and 1:1, preferably between 15:1 and 5:1, more preferably between 6:1 and 12:1.

Preferably, per 100% of its weight, the composition comprises:
From 0.01 to 10 weight %, preferably 0.1 to 5 weight % of additional compound.
From 0.01 to 10 weight %, preferably 0.1 to 5 weight % of surfactant.
From 80 to 99.98 weight %, preferably 90 to 99.8 weight % of flocculant.

In another aspect, the invention concerns a method for preparing a flocculation formulation, comprising the following steps:
preparing an aqueous phase comprising at least one anionic monomer and at least one nonionic monomer;
gel polymerizing the monomers of the aqueous phase;
obtaining a copolymer in gel form;
grinding the gel obtained in the presence of at least one additional compound and at least one surfactant.

Gel polymerization is a polymerization technique well known to skilled persons whereby water-soluble monomers are polymerized in an aqueous medium to obtain a gel which is then generally chopped or cut up and dried to obtain a powder polymer.

The gel is converted to a powder in conventional manner, for example by cutting the gel mass into pieces and/or extruding a gel mass through coarse openings, optionally cutting the gel before or after extrusion, and then drying the gel pieces as is conventional e.g. by heating.

As previously indicated, the preparation of the flocculation agent is obtained by gel polymerization. Post-hydrolysis or co-hydrolysis of the formed polymer is also possible. Preferably, polymerization is free-radical polymerization via gel route. Free-radical polymerization can include polymerization by free radicals generated by means of UV, azo, redox or thermal initiators as well as controlled radical polymerization (CRP) or matrix polymerization techniques.

The polymerization initiators used can be all compounds which break up into radicals under polymerization conditions, for example: organic peroxides, hydroperoxides, hydrogen peroxide, persulfates, azo compounds and redox catalysts. The use of water-soluble initiators is preferred. In some cases, it is advantageous to use mixtures of various polymerization initiators, for example mixtures of redox catalysts and azo compounds.

Suitable organic peroxides and hydroperoxides are for example sodium or potassium peroxydisulfate, acetylacetone peroxide, methylethylketone peroxide, tert-butyl hydroperoxide, cumene hydroperoxide, tert-amyl perpivalate, tert-butyl perpivalate, tert-butyl perneohexanoate, tert-butyl perbuto-butylate, ethyl hexanoate, tert-butyl perisononanoate, tert-butyl permaleate, tert-butyl peroxybenzoate, tert-butyl peroxy-3,5,5-trimethylhexanoate and tert-amyl perneodecanoate.

Suitable persulfates can be selected from among persulfates of alkali metals such as sodium persulfate.

Suitable azo initiators are advantageously water-soluble and selected from the following list: 2,2'-azobis-(2-amidinopropane) dihydrochloride, 2,2'-azobis (N, N'-dimethylene isobutyramidine) dihydrochloride, 2-(azo(1-cyano-1-methylethyl))-2-methylpropane nitrile, 2,2'-azobis [2-(2'-imidazolin-2-yl) propane] dihydrochloride and 4,4'-azobis (4-cyanovaleric acid). Said polymerization initiators are used in the usual amounts, for example in amounts of 0.001 to 2%, preferably 0.01 to 1% by weight relative to the monomers to be polymerized.

As oxidizing component, redox catalysts contain at least one of the aforementioned compounds, and as reducing agent for example ascorbic acid, glucose, sorbose, hydrogen sulfite, sulfite, thiosulfate, hyposulfite, pyrosulfite or an alkali metal, metal salts such as in the form of iron(II) ions or silver ions or sodium hydroxymethyl sulfoxylate. The reducing component of the redox catalyst used is preferably Mohr's salt (NH4)2Fe(SO4)2, 6 H2O. On the basis of the quantity of monomers used for polymerization, from $5\times10^{-6}$ to 1 mole of the reducing component of the redox catalyst system and from $5\times10^{-5}$ to 2 mole % of the oxidizing component of the redox catalyst are used. Instead of the oxidizing component of the redox catalyst, one or more water-soluble azo initiators can also be used.

In the method of the invention, the total weight concentration of free monomers relative to the polymerization feed is between 10 and 60%, advantageously between 20 and 55 and further advantageously between 25 and 50%.

In the invention, the monomers and different polymerization additives are dissolved, for example in vessels under stirring, in the aqueous medium to be polymerized. This solution, also called polymerization feed, is adjusted to an initiation temperature of between −20° C. to 50° C. Advantageously, this initiation temperature is adjusted to between −5° C. and 30° C. and further advantageously to between 0 and 20° C.

On completion of the reaction, the product derived from polymerization is a hydrated gel that is so viscous that it is self-supporting (for example a cube of gel with sides of 2.5 cm substantially keeps its shape when placed on a flat surface). The gel obtained is a viscoelastic gel.

It is to be noted that when the reaction is conducted in a reactor, to facilitate release of the gel after the reaction, the reactor is advantageously of upturned conical tube shape (downward-facing cone), to release the gel downwardly by applying a pressure of inert gas or air onto the gel surface, or in the form of a pivoting reactor to unload the gel mass by tilting the reactor.

The polymer obtained can be pre-added to water or another solvent before use. It can also be used in powder form.

The water solubility of a monomer refers to the capacity thereof to be dissolved in water under conventional conditions of gel polymerization.

The additional compound and the surfactant are added separately or simultaneously. They can be added before and/or during and/or after polymerization. Preferably, the additional compound and the surfactant are added after polymerization and before the grinding step.

In a further aspect, the invention provides a method for treating an aqueous effluent comprising solid particles, which comprises adding the flocculation formulation to the aqueous effluent.

In the invention, the effluent is advantageously mining extraction effluent, preferably from mined bituminous sand or oil sand extraction. In addition to solid particles, the effluent comprises water. It may contain sand, clay and water, or sand, clay, water and residual bitumen.

In general, the aqueous effluent of the invention comprises from 5 to 70 weight %, preferably 20 to 50 weight %, more preferably 30 to 40 weight % of solid particles, in particular mineral particles.

The effluent treated with the method of the invention may comprise different tailings. These tailings can be fresh tailings or fine tailings. Preferably, it is an effluent comprising mature fine tailings (MFT), in particular an effluent comprising mature fine tailings (MFT) with a clay content ranging from 5 to 70 weight %.

In general, the aqueous effluent derived from mining operations of bituminous sands and treated with the method of the invention, may also comprise residual bitumen. The residual bitumen is then contained in small amount, generally in an amount of less than 5 weight % of aqueous effluent.

Preferably, for the method of the invention, the flocculating agent is added in a weight amount of 10 to 10 000 ppm relative to the quantity of solid particles contained in the aqueous effluent. From a practical viewpoint, it is added in an amount ranging from 10 to 10 000 g per tonne of solid particles contained in the aqueous effluent.

The different aspects of the invention are illustrated in the following examples and Figures.

EXAMPLES

Example 1: Preparation of a Flocculation Formulation (X) of the Invention Comprising an ACM/Sodium Acrylate Copolymer A 2000 ml beaker was charged with 555.5 g of deionized water, 627.4 g of acrylamide in 50 solution, 29.5 g of urea, 136.3 g of ice-cold acrylic acid, 151.3 g of a 50 weight % solution of sodium hydroxide at room temperature, which were mixed together.

This charge was cooled to between 0 and 5° C. and transferred to an adiabatic polymerization reactor. Nitrogen bubbling was carried out for 30 minutes.

1.05 g of 2,2'-azobisisobutyronitrile were then added to the reactor with 6.0 ml of 10 g/l sodium hypophosphite solution. The reaction was initiated through successive additions of 1.2 ml of 5 g/l tert-butyl hydroperoxide solution followed by 1.8 ml of 5 g/l solution of Mohr's salt.

After a few minutes the nitrogen feed was shut off and the reactor closed. The polymerization reaction took place for 5 hours reaching a final temperature of 90° C. The gel obtained was chopped in the presence of composition A containing an additional compound (Vammar D10) and a surfactant (sorbitan monolaurate) in a ratio of 9:1

Per 100 g of gel weighed in the chopper, the addition was made of 0.39 g of composition A (corresponding to a portion of 1 weight % Vammar D10 relative to the dry polymer).

The gel was chopped into particles having a size of between 1 and 6 mm.

The gel was then dried and ground to obtain the polymer in powder form.

Example 2: Preparation of a Flocculation Formulation (Counter-Example F1) Comprising an ACM/Sodium Acrylate Copolymer The same operating mode was applied as described in Example 1 with the exception that in the grinding composition Vammar D10 was replaced by l'Exxsol D120 in the same ratio.

Per 100 g of gel weighed in the chopper, the addition was made of 0.39 g of the composition (corresponding to a portion of 1 weight % Exxsol D120 relative to the dry polymer).

Example 3: Preparation of a Flocculation Formulation (Counter-Example F2) Comprising an ACM/Sodium Acrylate Copolymer The same operating mode was applied as described in Example 1, with the exception that in the grinding composition Vammar D10 was replaced by Radiasurf 7443 in the same ratio.

Per 100 g of gel weighed in the chopper, the addition was made of 0.39 g of composition (corresponding to a portion of 1% Radiasurf 7443 relative to the dry polymer).

Protocols and Testing of the Different Formulations
Production Water

The production water used was derived from recovery of bitumen using the Clark hot water extraction process with sodium hydroxide. This process is known to generate natural surfactants capable of promoting detachment of bitumen from mineral surfaces thereby increasing recovery levels.

In the production water used we measured a content of 80 µl equivalents/L of electronegative colloids, which corresponds to the presence of residual anionic surfactants such as naphthenic acids generated when recovering bitumen.

Foaming Tests 1.5 g of polymer powder obtained was solubilized in 300 g of production water to prepare a 0.5 weight % solution of polymer. After complete dissolution, the polymer solution was poured in a foaming cell. This was composed of a plastic cylinder with centimetre graduation. A piece of sintered porous stone connected to an air inlet was placed in the bottom of the foaming cell. The chronometer was set in operation at the same time as the air stream. For 1 minute, the foam level was measured every 10 seconds, then every 30 seconds until the end of the test (5 minutes). It is noted that 3 cm corresponds to the level of the polymer solution in the cylinder before opening the air stream.

Figure 1:
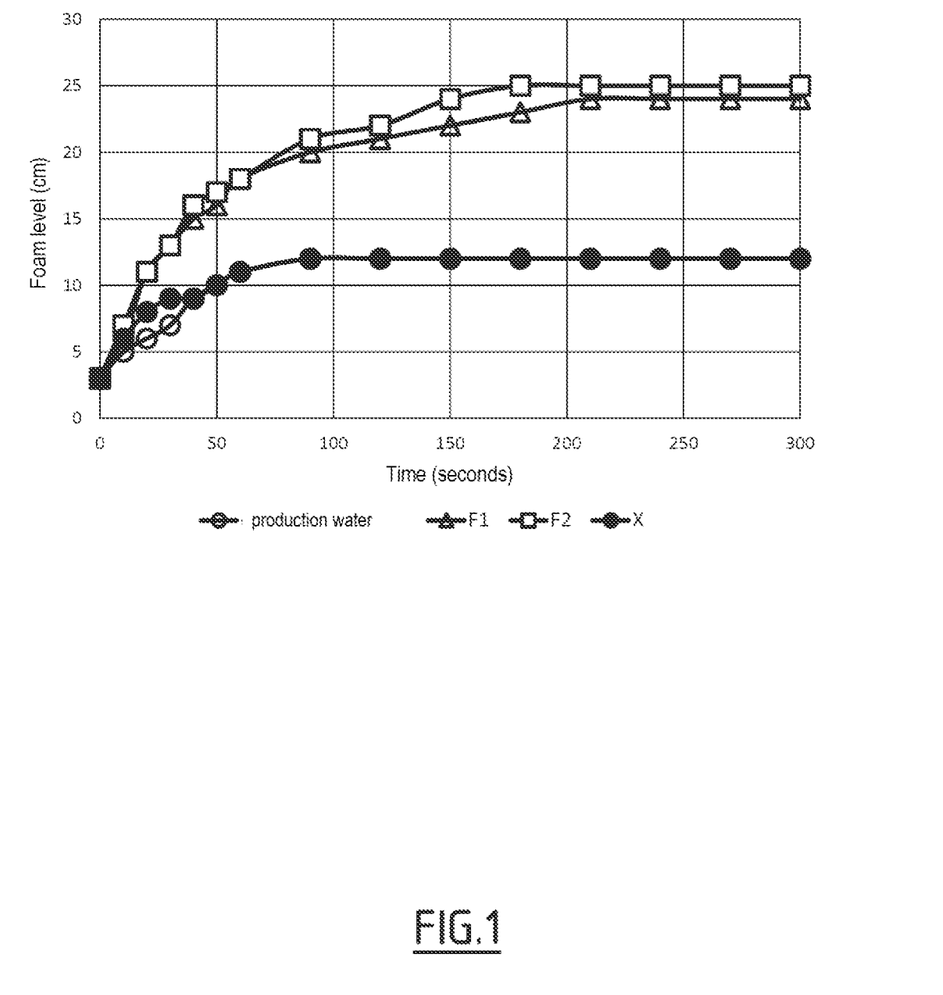
FIG. 1 gives foam levels as a function of time for different polymers.

The results given in FIG. 1 show that the production water used alone generates much foam and reached a stable foam level of 12 cm after 90 seconds. It can be seen that the formulations F1 and F2 lead to abundant foam since foam levels of 22-25 cm were reached after 150-200 seconds. Formulation X allowed a signification reduction in the foam level to only 12 cm, which corresponds to the level reached by the production water alone.

Drainage Tests on Flocculated Slurries

The «4-inch vessel» procedure developed by Suncor (IOSTC—International Oil Sands Tailings Conference—2018, pages 81-92, Edmonton, AB—Dec. 9-12, 2018) was used to evaluate the technical performance of the flocculants. For each test, 400 g of effluent were poured into a vessel 4 inches in diameter (i.e. about 10 cm). The desired amount of formulation was injected therein under constant stirring of 200 rpm until the medium appeared to be visibly thicker. At this time, stirring was decreased to 50 rpm and stopped when water release was observed. The same mixing sequence was applied for each test: 30 seconds at 200 rpm followed by 30 seconds at 50 rpm.

The flocculated effluent was poured through a 1 mm screen on which it drained for 24 h to measure Net Water Release (NWR), filtrate dry extract (FDE) and flocculated portion dry extract (FPDE).

NWR=Net Water Release. This corresponds to the total amount of water recovered during the flocculation test less the amount of water unduly added when incorporating the aqueous polymeric solution and dispersant solution in the suspension.

Figure 2:
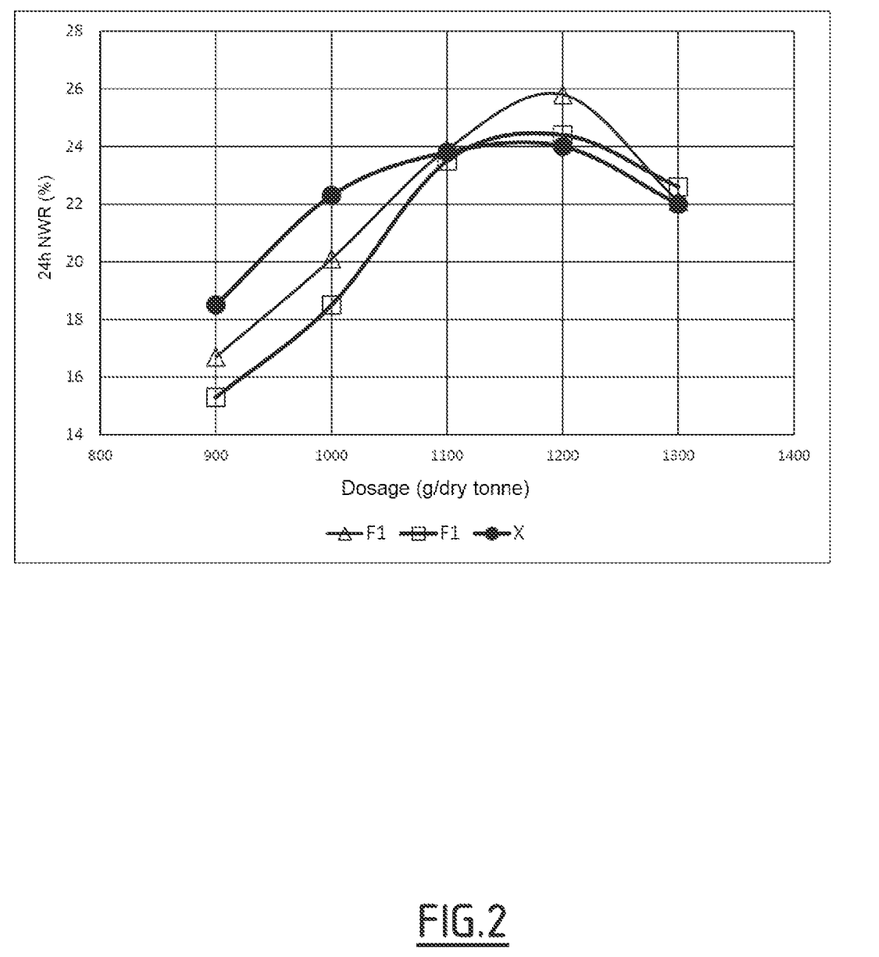
FIG. 2 gives Net Water Release as a function of the dosage of different polymers.
Figure 3:
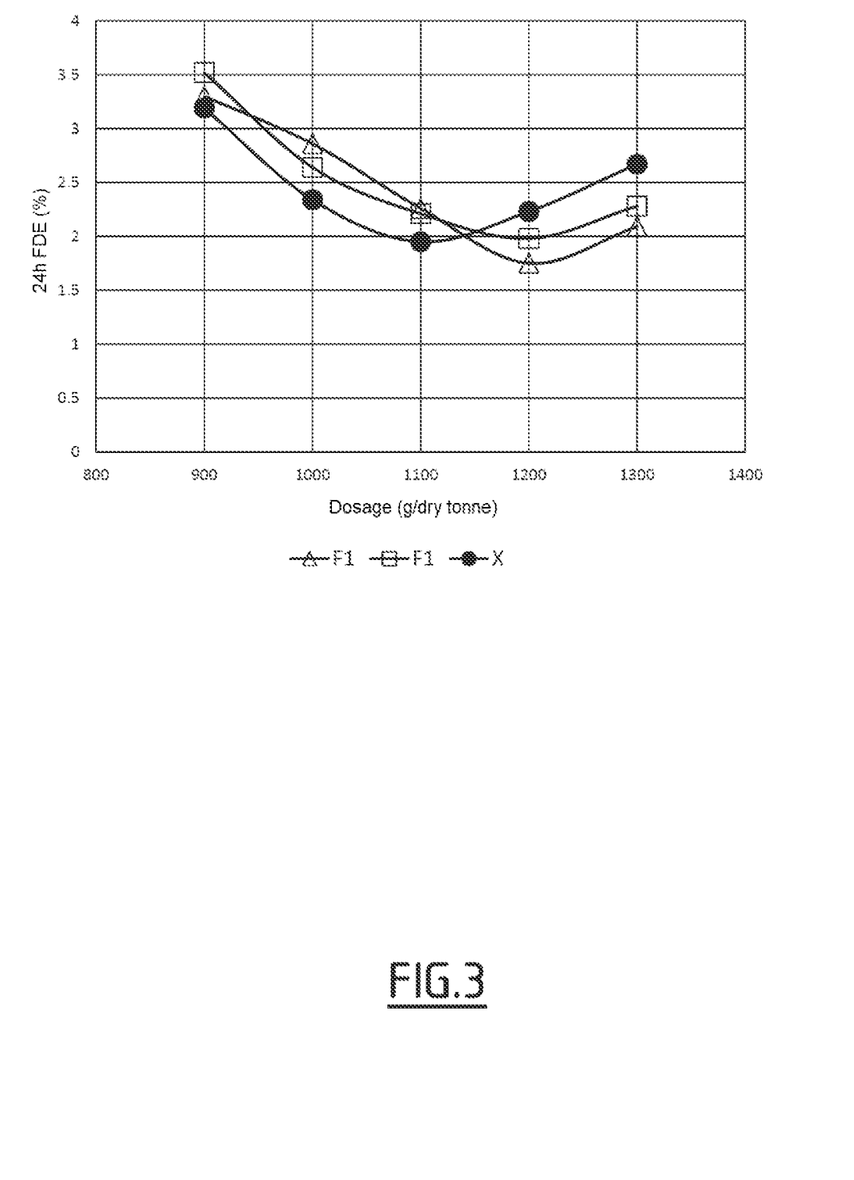
FIG. 3 gives the dry extract of the filtrate as a function of the dosage of different polymers.
Figure 4:
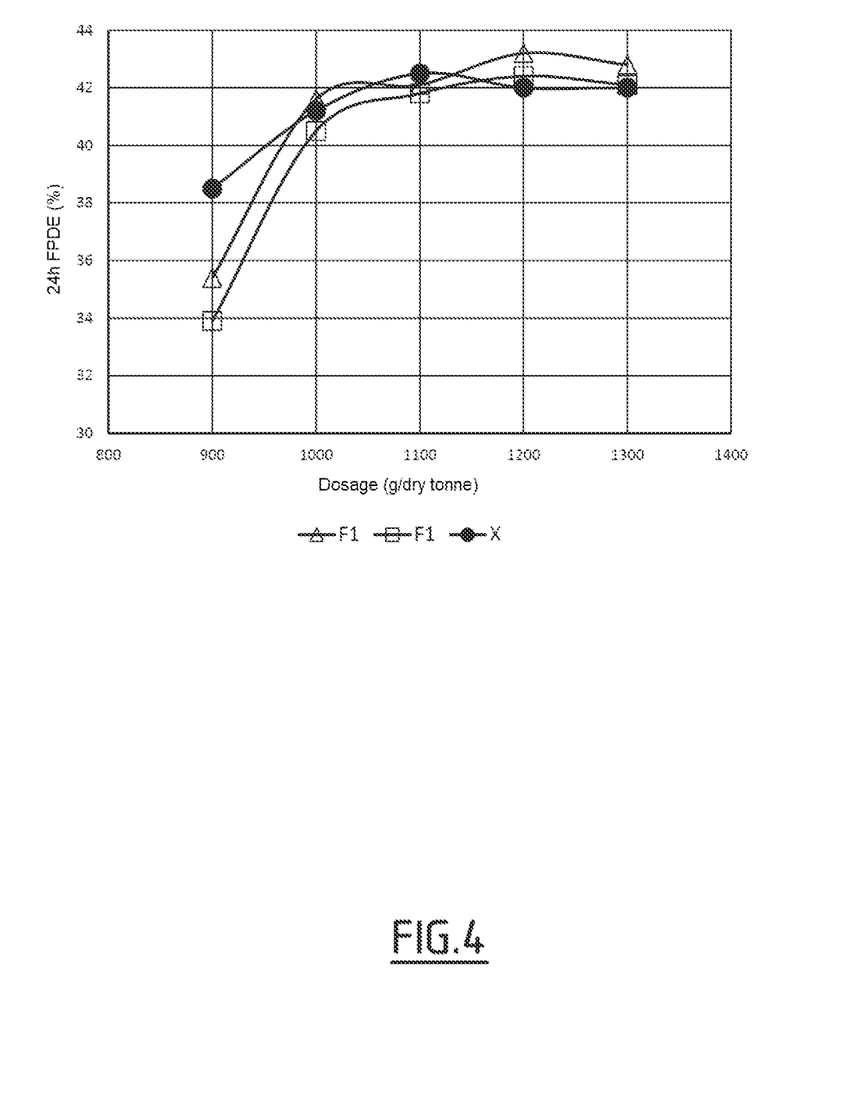
FIG. 4 gives the dry extract of the flocculated portion as a function of the dosage of different polymers.

As expected, formulations F1 and F2 after 24 h led to the same values of NWR, FDE and FPDE. Formulation X also led to similar results without impacting the flocculation process (FIG. 2). Optimal dosage in the region of 1000-1200 g/dry tonne led to:
- 24 h NWR of about 24-26%;
- 24 h FDE of about 1.8-2%;
- 24 h FPDE of about 40-44%.

The invention claimed is:

1. A flocculation formulation comprising:
   from 80 to 99.98 weight percent of at least one flocculating agent, said agent being a copolymer prepared from at least one nonionic monomer and at least one anionic monomer, said copolymer being in powder form;
   from 0.01 to 10 weight percent of at least one surfactant, wherein said surfactant is a fatty acid ester;
   from 0.01 to 10 weight percent of at least one additional compound having formula (I):

Formula I where:
   R1 is a hydrogen atom or a saturated or unsaturated, linear, branched, aromatic or cyclic carbon radical having X carbon atoms of between 3 and 20; wherein said carbon radicals are radical chains comprising only carbon atoms and hydrogen atoms
   R2 is a saturated or unsaturated, linear, branched, aromatic or cyclic carbon radical having Y carbon atoms of between 3 and 20; and
   X+Y=6 to 30 carbon atoms.

2. The formulation according to claim 1, wherein the nonionic monomer is selected from among acrylamide, methacrylamide; N-isopropylacrylamide; N,N-dimethylacrylamide; N, N diethylacrylamide; N-methylolacrylamide N-vinylformamide; N-vinyl acetamide; N-vinylpyridine; N-vinylpyrrolidone; acryloyl morpholine (ACMO), glycidyl methacrylate, glyceryl methacrylate and diacetone acrylamide.

3. The formulation according to claim 1, wherein the anionic monomer is selected from among acrylic acid, methacrylic acid, itaconic acid, crotonic acid, maleic acid, fumaric acid, 2-acrylamido-2-methylpropanesulfonic acid, vinylsulfonic acid, vinylphosphonic acid, allylsulfonic acid, allylphosphonic acid, styrenesulfonic acid and the corresponding water-soluble salts.

4. The formulation according to claim 1, wherein the copolymer has a molecular weight ranging from 3 to 40 million g/mol.

5. The formulation according to claim 1, wherein the surfactant is a fatty acid ester selected from the group consisting of sorbitan monostearate, sorbitan tristearate, sorbitan monolaurate, sorbitan monooleate, sorbitan monopalmitate, sorbitan trioleate, and mixtures thereof.

6. The formulation according to claim 1, wherein in the additional compound X+Y is between 8 and 28.

7. The formulation according to claim 1, wherein the additional compound comprises at least 2 different compounds of formula (II) and (III):

Formula II where m and m' are equal or differ, and are each between 3 and 9, and Formula III where n is between 5 and 8.

8. The formulation according to claim 1, wherein the additional compound/surfactant ratio is between 20:1 and 1:1, preferably between 15:1 and 5:1.

9. The formulation according to claim 1, wherein the amount of additional compound is between 0.1 and 10 weight % relative to the dry flocculating agent.

10. A method for preparing a flocculation formulation according to claim 1, comprising:
   preparing an aqueous phase comprising at least one anionic monomer and at least one nonionic monomer;
   gel polymerizing the monomers of the aqueous phase;
   obtaining a copolymer in gel form;
   grinding the gel obtained in the presence of at least one additional compound having formula (I) and at least one surfactant, wherein said surfactant is a fatty acid ester.

11. A method for treating an aqueous effluent comprising solid particles, comprising the addition of the flocculation formulation according to claim 1 to the aqueous effluent.

12. The method for treating an aqueous effluent according to claim 11, wherein the aqueous effluent is effluent from mined bituminous sand or oil sand extraction.

* * * * *